(12) United States Patent
Marinelli et al.

(10) Patent No.: US 7,455,455 B2
(45) Date of Patent: Nov. 25, 2008

(54) PATIENT BARRIER FOR AN IMAGING APPLICATION

(75) Inventors: Nicholas Louis Marinelli, Wauwatosa, WI (US); Rowland Frederick Saunders, Hartland, WI (US); Lawrence E. Murphy, Shorewood, WI (US); Atul Tandon, New Berlin, WI (US)

(73) Assignee: General Electric Company, Schenectady, NY (US)

( * ) Notice: Subject to any disclaimer, the term of this patent is extended or adjusted under 35 U.S.C. 154(b) by 255 days.

(21) Appl. No.: 11/391,784

(22) Filed: Mar. 29, 2006

(65) Prior Publication Data

US 2007/0237309 A1    Oct. 11, 2007

(51) Int. Cl.
*A61B 6/04* (2006.01)
(52) U.S. Cl. .................................... 378/208
(58) Field of Classification Search ............. 378/208, 378/195, 196
See application file for complete search history.

(56) References Cited

U.S. PATENT DOCUMENTS 2,886,096 A  *  5/1959  Eckart et al. ................ 297/80
3,927,326 A  *  12/1975  Kunne et al. ................ 378/195
4,287,422 A  *  9/1981  Kuphal et al. ............... 378/209
5,042,487 A  *  8/1991  Marquardt ................... 378/196
6,282,264 B1    8/2001  Smith et al.
6,901,159 B2    5/2005  Baertsch et al.
7,264,396 B2 *  9/2007  Jahrling ...................... 378/195
2001/0022833 A1* 9/2001  Kobayashi .................. 378/209
2003/0123616 A1* 7/2003  Jackson, Sr. ................ 378/209

FOREIGN PATENT DOCUMENTS

JP           02220398 A   *  9/1990

* cited by examiner

*Primary Examiner*—Chih-Cheng G Kao
(74) *Attorney, Agent, or Firm*—Armstrong Teasdale LLP

(57) ABSTRACT

A patient barrier is described. The patient barrier includes a footstep configured to support a patient and placed on a floor, a frame attached to the footstep and configured to separate the patient from an energy receptor The patient barrier includes at least one of a first pivot configured to pivot the patient barrier with respect to the floor, and a support bar coupled to the frame, configured to support an arm of the patient, and pivot with respect to the frame.

19 Claims, 6 Drawing Sheets

PATIENT BARRIER FOR AN IMAGING APPLICATION

BACKGROUND OF THE INVENTION

This invention relates generally to medical imaging systems, and more particularly, to a patient barrier for supporting a subject during a medical examination.

Medical imaging is a specialty that uses radiation, such as gamma rays, x-rays, high-frequency sound waves, magnetic fields, neutrons, or charged particles to produce a plurality of images of internal body structures. In diagnostic radiology, radiation is used to detect and diagnose disease, while in interventional radiology, radiation is used to treat disease and bodily abnormalities.

Radiography is the technique of producing a radiographic image of any opaque specimen by the penetration of radiation, such as gamma rays, x-rays, neutrons, or charged particles. When a beam of radiation is transmitted through any heterogeneous object, the radiation is differentially absorbed depending upon varying object thickness, density, and chemical composition. The radiation emergent from a subject forms the radiographic image, which may then be realized on an image detection medium, such as photographic film directly or by using a phosphor to first create a light image. Radiography is a non-destructive technique of testing a gross internal structure of the subject, and is conventionally used in medical and industrial applications. Radiography is used to non-destructively detect medical conditions such as tuberculosis and bone fractures, as well as manufacturing imperfections in materials such as cracks, voids, and porosities.

During the medical imaging of the subject, the subject may not be in a stable position. If the subject is not in a stable position, a plurality of artifacts are generated within the radiographic image.

BRIEF DESCRIPTION OF THE INVENTION

A patient barrier is described. The patient barrier includes a footstep configured to support a patient and placed on a floor, a frame attached to the footstep and configured to separate the patient from an energy receptor The patient barrier includes at least one of a first pivot configured to pivot the patient barrier with respect to the floor, and a support bar coupled to the frame, configured to support an arm of the patient, and pivot with respect to the frame.

An X-ray imaging system is described. The x-ray imaging system includes an x-ray source, an x-ray receptor, and a patient barrier. The patient barrier includes a footstep configured to support a patient and placed on a floor, a frame attached to the footstep and configured to separate the patient from an energy receptor. The patient barrier includes at least one of a first pivot configured to pivot the patient barrier with respect to the floor, and a support bar coupled to the frame, configured to support an arm of the patient, and pivot with respect to the frame.

An X-ray imaging system is described. The x-ray imaging system includes an x-ray source, an x-ray receptor, and a patient barrier. The patient barrier includes a footstep configured to support a patient and placed on a floor, a frame attached to the footstep, made from at least one of a metal and a plastic, and configured to separate the patient from an energy receptor. The patient barrier includes a first pivot configured to pivot the patient barrier with respect to the floor.

DETAILED DESCRIPTION OF THE INVENTION

Figure 1:
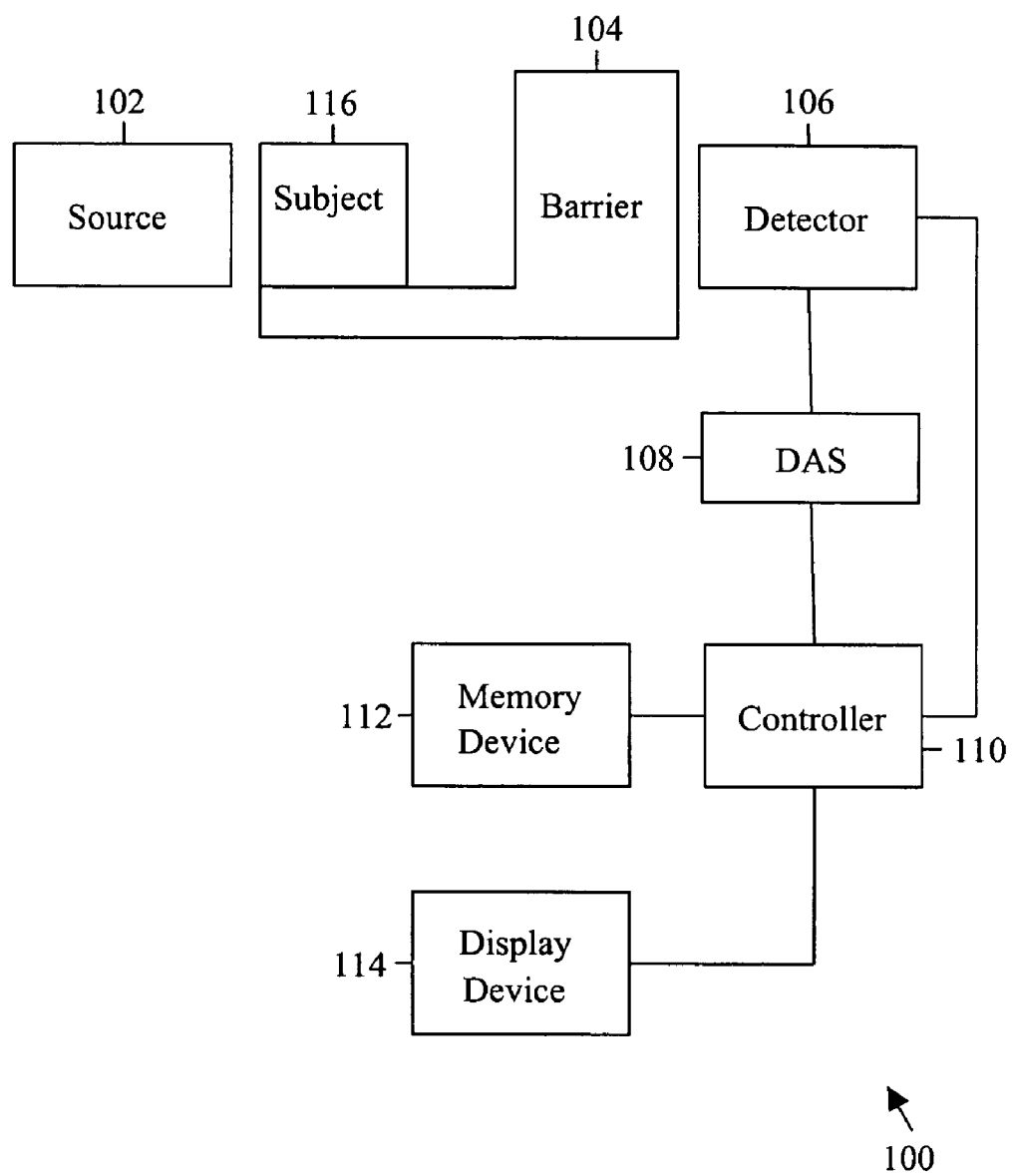
FIG. 1 is a block diagram illustrating an embodiment of an imaging system.

FIG. 1 is a block diagram illustrating an embodiment of an imaging system 100. Imaging system 100 includes a source 102, a barrier 104, a receptor or detector 106, a data acquisition system (DAS) 108, a controller 110, a memory device 112, and a display device 114. Examples of source 102 include a gamma ray source and an x-ray source. Further, detector 106 may include a film cassette or alternatively may include a digital flat panel detector. As used herein, the term controller is not limited to just those integrated circuits referred to in the art as a controller, but broadly refers to a computer, a processor, a microcontroller, a microcomputer, a programmable logic controller, an application specific integrated circuit, and other programmable circuits, and these terms are used interchangeably herein. Memory device 112 may be a volatile memory or a non-volatile memory. Examples of display device 114 includes a liquid crystal display and a cathode ray tube.

Source 102 generates radiation, such as x-rays or alternatively gamma rays, that passes through a subject 116, such as a patient, and is detected by detector 106. If detector 106 includes the film cassette, detector 106 generates a radiation image, such as an x-ray image or alternatively a gamma ray image. Alternatively, if detector 106 is the digital flat panel detector that includes a scintillator array and a photodiode array, detector 106 generates a plurality of analog electrical signals. DAS 108 receives the analog electrical signals, amplifies the analog electrical signals, and converts the analog electrical signals into a plurality of digital signals. Controller 110 generates a radiation image, such as an x-ray image or alternatively a gamma ray image, from the digital signals, displays the radiation image on display device 114, and stores the radiation image in memory device 112.

Figure 2:
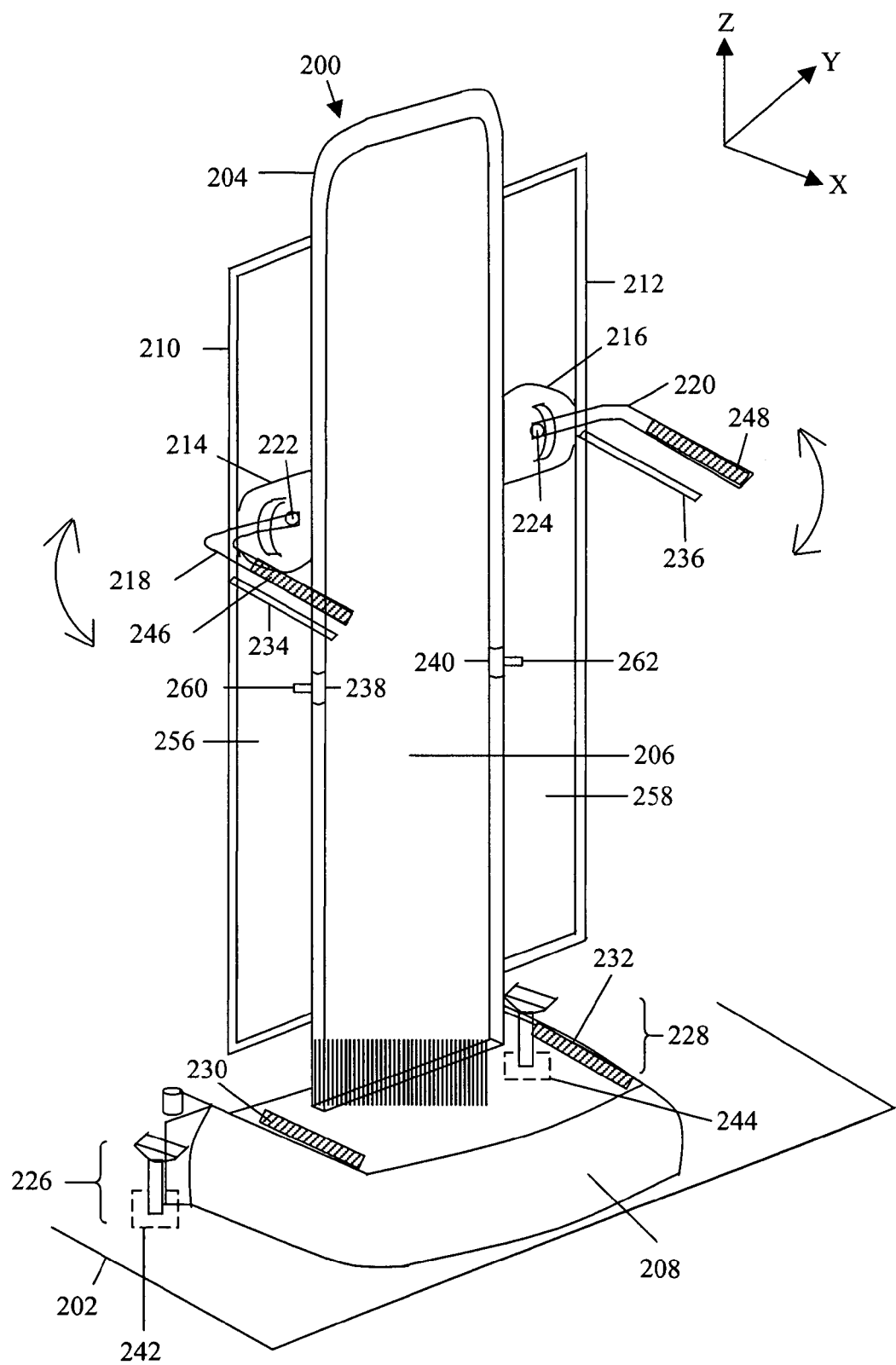
FIG. 2 is an isometric view of an embodiment of a barrier of the system of FIG. 1.
Figure 3:
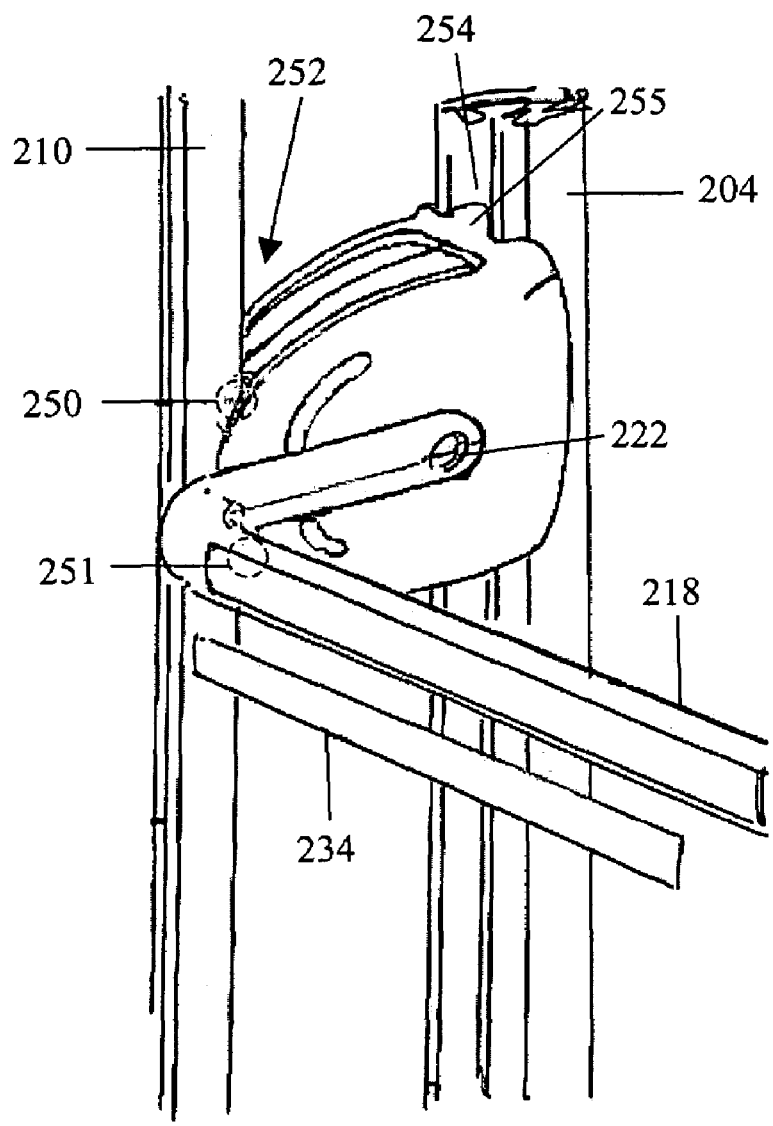
FIG. 3 is an isometric view of a portion of the barrier.

FIG. 2 is an isometric view of an embodiment of barrier 200. FIG. 3 is an isometric view of a portion of barrier 200. Barrier 200 is placed on a floor 202 and includes a frame 204, a screen 206, a footstep 208, a plurality of handles 210 and 212, a plurality of hubs 214 and 216, a plurality of support bars 218 and 220, a plurality of pivots 222, 224, 226, and 228, a plurality of rulers 230, 232, 234, and 236, and a plurality of locks 238 and 240. A user places footstep 208 on floor 202. A plurality of holes 242 and 244 are formed within floor 202. Pivots 226 and 228 are attached, such as welded, bolted, and/or glued, to footstep 208. The user inserts pivots 226 and 228 in holes 242 and 244. In an alternative embodiment, pivot 226 is inserted within hole 242 formed within a surface plate and pivot 228 is inserted within hole 244 formed within a surface plate. The surface plates may be fabricated from a material, such as, plastic, carbon, and/or metal.

Each of frame 204, handles 210 and 212, footstep 208, hubs 214 and 216, support bars 218 and 220, locks 238 and 240, and pivots 222, 224, 226, and 228 are fabricated from a material, such as, plastic, carbon, and/or metal, which may be steel or aluminum. For example, footstep 208 is fabricated from a composite, such as, a composite of graphite and plastic. As another example, footstep 208 is fabricated from an alloy. Screen 206 is made of a material, such as a radiotranslucent non-attenuating material, such as polyester.

Rulers 230 and 232 are attached, such as glued and/or bolted, to footstep 208. A hand grip 246 made of a material, such as, rubber or plastic, is attached, such as glued and/or bolted, to support bar 218. Another hand grip 248 made of a material, such as, rubber or plastic, is also attached, such as glued and/or bolted, to support bar 220. Frame 204 is attached, such as glued, bolted, and/or welded, to footstep 208. Moreover, handle 210 is attached, such as glued, bolted, and/or welded, to frame 204. Furthermore, handle 212 is attached, such as glued, bolted, and/or welded, to frame 204.

Hub 214 is slidably attached to frame 204 and handle 210. For example, hub 214 is attached via a plurality of rollers 250 and 251 to handle 210 and attached via a plurality of rollers, such as rollers 250 and 251, to frame 204. More than two, such as three or alternatively four, rollers may be used to slidably attach hub 214 to frame 204 and to more than two rollers may be used to slidably attach hub 214 to handle 210. Hub 216 is slidably attached to frame 204 and handle 212. As an example, hub 216 is attached via a plurality of rollers, such as rollers 250 and 251, to handle 212 and via a plurality of rollers, such as rollers 250 and 251, to frame 204. More than two, such as three or alternatively four, rollers may be used to slidably attach hub 216 to frame 204 and to more than two rollers may be used to slidably attach hub 216 to handle 212.

At least a portion of rollers 250 and 251 between hub 214 and handle 210 is located within a channel or slot 252 formed within handle 210. Similarly, at least a portion of the rollers between hub 216 and handle 212 is located within a channel or slot formed within handle 212. Moreover, at least a portion of the rollers between hub 214 and frame 204 is located within a channel or slot 254 formed within frame 204. Slot 254 extends along a circumference of frame 204. Similarly, at least a portion of the rollers between hub 216 and frame 204 is located within slot 254 of frame 204. In an alternative embodiment, hub 214 is slidably attached to slot 254 via a protrusion 255 of hub 214. Protrusion 255 extends into slot 254 during a sliding motion of hub 214. Similarly, in an alternative embodiment, hub 216 is slidably attached to slot 254 via a protrusion of hub 216 and the protrusion extends into slot 254 during a sliding motion of hub 216.

Hub 214 slides along a z-direction in a space or gap 256 formed between frame 204 and handle 210, and hub 216 slides along the z-direction in a space or gap 258 formed between frame 204 and handle 212. In an alternative embodiment, barrier 200 may not include at least one of handles 210 and 212. The z-direction includes a positive z-direction and a negative z-direction.

Locks 238 and 240 that are frictionally affixed with frame 204 includes a plurality of protrusions 260 and 262. In an alternative embodiment, locks 238 and 240 are bolted to frame 204. In another alternative embodiment, lock 238 is attached, such as by friction or bolted, to handle 210. In another alternative embodiment, lock 240 is attached, such as by friction or bolted, to handle 212. Protrusion 260 prevents hub 214 from sliding down in the negative z-direction and protrusion 262 prevents hub 216 from sliding in the negative z-direction. Positions of locks 238 and 240 are changed in the z-direction by detaching the locks 238 and 240 from frame 204 to remove a frictional fit with frame 204, re-attaching lock 238 to frame 204, and re-attaching lock 240 to frame 204. Lock 238 is re-attached to frame 204 to form a frictional fit within frame 204 and lock 240 is re-attached to frame 204 to form a frictional fit with frame 204. In an alternative embodiment, a position of lock 238 is changed in the z-direction by unattaching, such as unbolting, lock 238 from frame 204 and then attaching, such as bolting, lock 238 to frame 204. In another alternative embodiment, a position of lock 240 is changed in the z-direction by unattaching, such as unbolting, lock 240 from frame 204 and then attaching, such as bolting, lock 240 to frame 204.

Support bar 218 pivots with respect to hub 214 and frame 204, and support bar 220 pivots with respect to hub 216 and frame 204. Support bar 218 pivots with respect to hub 214 in either a clockwise or a counterclockwise direction. Support bar 220 pivots with respect to hub 216 in either a clockwise or a counterclockwise direction. Pivot 222 is slidably attached to hub 214 and pivot 222 is attached, such as glued, welded, and/or bolted, to support bar 218. Pivot 224 is slidably attached to hub 216 and pivot 224 is attached, such as glued, welded, and/or bolted, to support bar 220.

Figure 4:
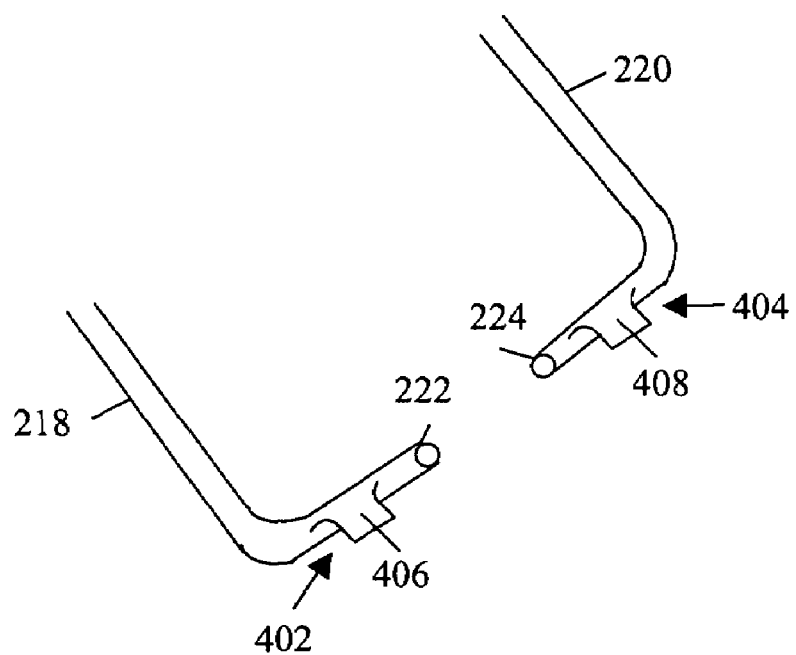
FIG. 4 illustrates an embodiment of a locking mechanism used to lock a support bar of the barrier.
Figure 5:
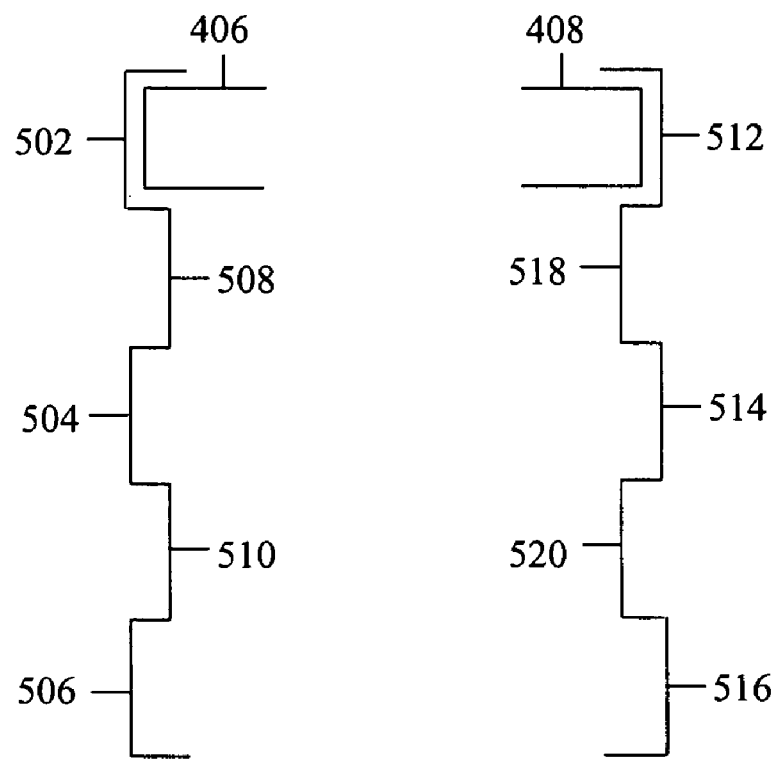
FIG. 5 illustrates the remaining portion of the locking mechanism.

FIGS. 4 and 5 illustrate an embodiment of a locking mechanism 402 used to lock support bar 218 in a position with respect to hub 214 and a locking mechanism 404 used to lock support bar 220 in a position with respect to hub 216. Locking mechanism 402 includes a protrusion 406, which is a portion of support bar 218 and locking mechanism 404 includes a protrusion 408, which is a portion of support bar 220. Locking mechanism 402 also includes a plurality of channels or slots 502, 504, and 506 formed within hub 214. Protrusion 406 fits within one of slots 502, 504, and 506. For example, protrusion 406 fits within slot 502. In the example, when support bar 218 moves either clockwise or counterclockwise with respect to hub 214, protrusion 406 slides from slot 502 to slot 504 and fits within slot 504. Slots 502 and 504 are separated by protrusion 508 and slots 504 and 506 are separated by a protrusion 510. Support bar 218 locks at a position in which protrusion 406 fits within one of slots 502, 504, and 506.

Locking mechanism 404 also includes a plurality of channels or slots 512, 514, and 516 formed within hub 214. Protrusion 408 fits within one of slots 512, 514, and 516. For example, protrusion 408 fits within slot 512. In the example, when support bar 220 moves either clockwise or counterclockwise with respect to hub 216, protrusion 408 slides from slot 512 to slot 514 and fits within slot 514. Slots 512 and 514 are separated by a protrusion 518 and slots 514 and 516 are separated by a protrusion 520. Support bar 220 locks at a position in which protrusion 408 fits within one of slots 512, 514, and 516.

Referring back to FIGS. 2 and 3, screen 206 is attached, such as bolted and/or glued, to frame 204. In an alternative embodiment, a space or gap is formed between screen 206 and frame 204 and screen 206 suspends from frame 204. A distance between frame 204 and screen 206 when the gap is formed between frame 204 and screen 206 includes a range between one and five centimeters. Screen 206 separates subject 116 from detector 106. A height of footstep 208 in the z-direction from floor 202 facilitates imaging of subject 116 during scanning of all portions of legs of subject 116. An example of the height of footstep 208 ranges from and including six feet to ten feet. Further, rulers 230 and 232 are attached, such as bolted and/or glued, to footstep 208 for measuring a depth, in a x-direction, of a portion below an abdomen of subject 116. Similarly, ruler 234 is attached to handle 210 and ruler 236 is attached to handle 212 for measuring a depth, in the x-direction, of a portion of subject 116 and the portion includes either the abdomen or is above the abdomen of subject 116. Footstep 208 may be covered with a non-slippery material, such as rubber, to prevent subject 116 from slipping when standing on footstep 208.

Subject 116 stands on footstep 208 and rests his/her arms on support bars 218 and 220. A height of hubs 214 and 216 from footstep 208 is adjusted so that arms of subject 116 lie on support bars 218 and 220 when the arms are extended laterally from subject 116. A height of hubs 214 and 216 is adjusted from footstep 208 by sliding hubs 214 and 216 along the z-direction. Hubs 214 and 216 are locked at a position so that arms of subject 116 lie on support bars 218 and 220 when the arms are extended laterally from subject 116. Hub 214 is locked by attaching lock 238 to frame 204 and resting hub 214 on lock 238. Moreover, hub 216 is locked by attaching lock 240 to frame 204 and resting hub 216 on lock 240.

An arm of subject 116 rests on support bar 218 that is locked at a position with respect to hub 214. Another arm of subject 116 rests on support bar 220 that is locked at a position with respect to hub 216. Alternatively, subject 116 may grab handles 210 and 212 instead of resting arms on support bars 218 and 220. A material, such as a ribbed rubber material, is attached, such as glued and/or bolted, to support bars 218 and 220 to provide a grip to subject 116. Source 102 generates the radiation and detector 106 is controlled by controller 110 to move in the z-direction to scan subject 116 and to generate a radiation image of subject 116.

Figure 6:
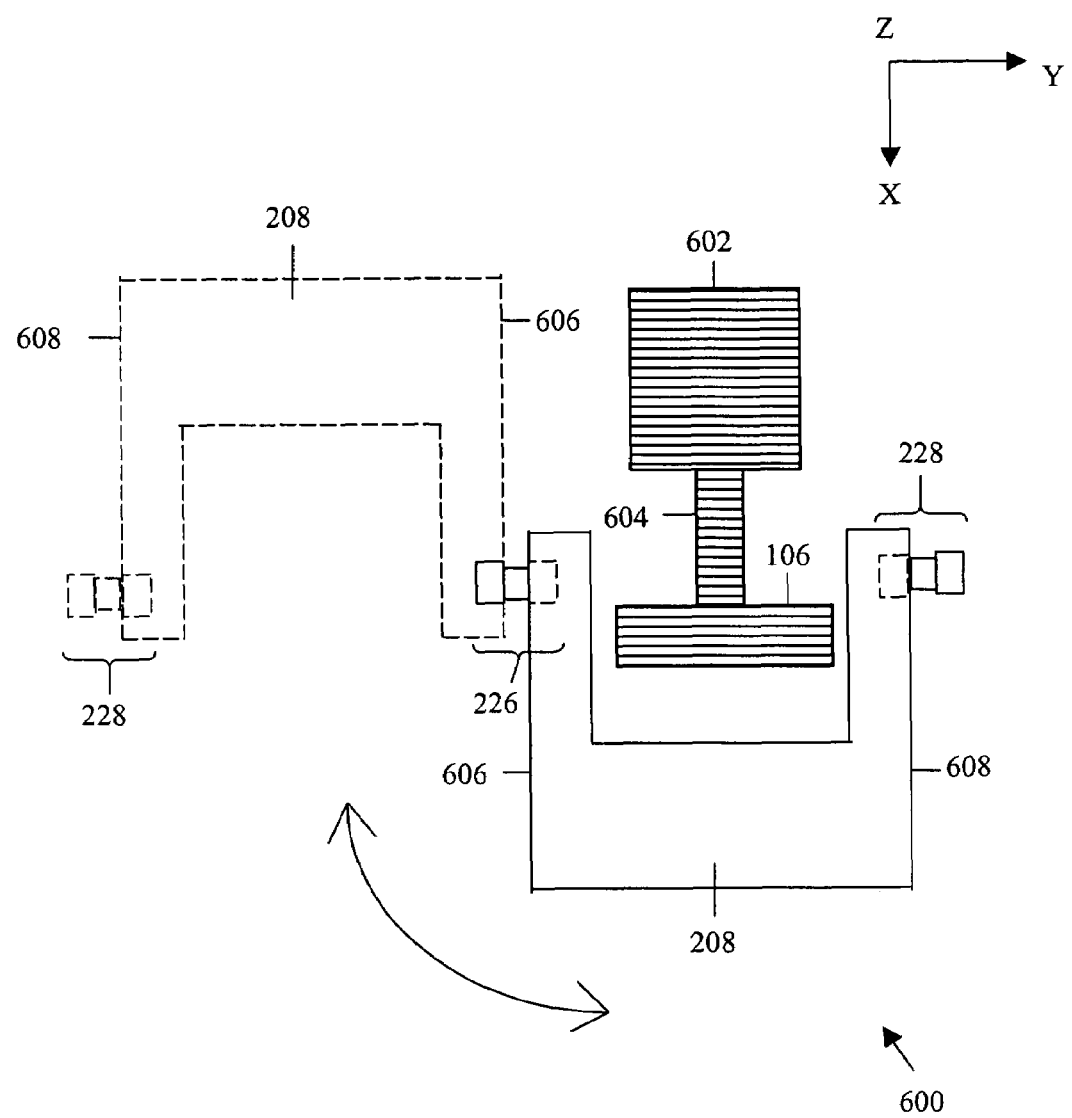
FIG. 6 illustrates a top view of an embodiment of a system including a footstep of the barrier.

FIG. 6 illustrates a top view of an embodiment of a system 600 including detector 106 and footstep 208. System 600 further includes a base 602 and a link 604. Detector 106 is attached to base 602 via link 604 and base 602 rests on floor 202. Controller 110 controls detector 106 to move detector 106 with respect to base 602. Pivot 226 is attached, such as, glued, welded, and/or bolted, to a surface 606 of footstep 208. Pivot 228 is attached, such as, glued, welded, and/or bolted, to a surface 608 of footstep 208. Pivot 226 is inserted into hole 242. The user removes a portion of pivot 226 extending within hole 242. The user slides footstep 208 and barrier 200 with respect to pivot 226 and floor 202 to change a position of barrier 200. The user slides footstep 208 and barrier 200 with respect to pivot 226 and floor 202 in either a clockwise or a counterclockwise direction. When the user slides footstep 208 with respect to pivot 226, pivot 226 is inserted into hole 242 within floor 202 and pivot 228 is outside hole 244. Portions of pivots 226 and 228 extending within holes 242 and 244 are removed from holes 242 and 244 to store barrier 200 in a place, such as a closet.

Technical effects of barrier 200 include providing pivots 226 and 228 to facilitate an easy removal and moving of barrier 200. Other technical effects include providing support bars 218 and 220 to support arms of subject 116 outward from a torso of subject 116 and to perform a scan of a spine of subject 116 from a lateral side of subject 116. Further technical effects include providing footstep 208 so that detector 106 can detect all portions of legs of subject 116. Additional technical effects include providing a stable barrier 200 that is temporarily attached to floor 202 via pivots 226 and 228. Barrier 200 provides a precise separation between subject 116 and detector 106. Other technical effects include pivoting support bars 218 and 220 to move support bars 218 and 220 away from or closer to a centerline of screen 206 to accommodate varied arm lengths. Yet other technical effects include reducing the chances of contact of subject 116 with any moving parts of detector 106 by placing barrier 104 between subject 116 and detector 106.

While the invention has been described in terms of various specific embodiments, those skilled in the art will recognize that the invention can be practiced with modification within the spirit and scope of the claims.

What is claimed is:

1. A patient barrier comprising:
   a footstep configured to support a standing patient, said footstep placed on a floor;
   a frame attached to said footstep and configured to separate the standing patient from an energy receptor, wherein said patient barrier comprises:
      a first pivot configured to pivot said patient barrier with respect to the floor; and
      a support bar coupled to said frame, configured to support an arm of the standing patient and pivot with respect to said frame.

2. A patient barrier in accordance with claim 1 wherein said first pivot is attached to said footstep, and said first pivot is configured to insert into one of the floor and a surface plate attached to the floor.

3. A patient barrier in accordance with claim 1 further comprising a hub slidably coupled within a slot defined in said frame.

4. A patient barrier in accordance with claim 1 further comprising:
   a hub slidably coupled within a slot defined in said frame; and
   a second pivot coupled to said hub and configured to pivot said support bar with respect to said frame.

5. A patient barrier in accordance with claim 1 further comprising a ruler attached to said footstep and configured to measure a depth of a portion of the patient below an abdomen of the patient.

6. A patient barrier in accordance with claim 1 further comprising a ruler attached to said support bar and configured to measure a depth of a portion including an abdomen of the patient.

7. A patient barrier in accordance with claim 1 further comprising a second pivot attached to said footstep and configured to insert into one of the floor and a first surface plate, wherein said patient barrier is configured to be removed by removing said first pivot from engagement from one of the floor and a second surface plate and by removing said second pivot from engagement from one of the floor and the first surface plate.

8. A patient barrier in accordance with claim 1 further comprising a screen coupled to said frame, said screen comprising a radiotranslucent non-attenuating material.

9. A patient barrier in accordance with claim 1 further comprising a handle coupled to said frame, wherein a space is formed between said handle and said frame.

10. A patient barrier in accordance with claim 1 further comprising:
    a handle coupled to said frame, wherein a space is formed between said handle and said frame;
    a hub slidably coupled within a slot defined in said frame and within a slot defined within said handle.

11. An X-ray imaging system comprising:
    an x-ray source;
    an x-ray receptor; and
    a patient barrier, said patient barrier comprising:
       a footstep configured to support a standing patient, said footstep placed on a floor;
       a frame attached to said footstep and configured to separate the standing patient from the x-ray receptor, wherein said patient barrier comprises:
          a first pivot configured to pivot said patient barrier with respect to the floor; and
          a support bar coupled to said frame, configured to support an arm of the standing patient and pivot with respect to said frame.

12. An X-ray imaging system in accordance with claim 11 wherein said first pivot is attached to said footstep, and said first pivot is configured to insert into one of the floor and a surface plate attached to the floor.

13. An X-ray imaging system in accordance with claim 11 further comprising a hub slidably coupled within a slot defined in said frame.

14. An X-ray imaging system in accordance with claim 11 further comprising:
   a hub slidably coupled within a slot defined in said frame; and
   a second pivot coupled to said hub and configured to pivot said support bar with respect to said frame.

15. An X-ray imaging system in accordance with claim 11 further comprising a ruler attached to said footstep and configured to measure a depth of a portion of the patient below an abdomen of the patient.

16. An X-ray imaging system comprising:
   an x-ray source;
   an x-ray receptor; and
   a patient barrier, said patient barrier comprising:
      a footstep configured to support a standing patient, said footstep placed on a floor;
      a frame attached to said footstep, said frame comprising at least one of a plastic and a metal, said frame configured to separate the standing patient from the x-ray receptor;
      a support bar configured to support an arm of the standing patient and coupled to said frame such that said support bar pivots with respect to said frame;
      a hub slidably coupled within a slot defined in said frame;
      a first pivot configured to pivot said patient barrier with respect to the floor; and
      a second pivot coupled to said hub and configured to pivot said support bar with respect to said frame.

17. An X-ray imaging system in accordance with claim 16 further wherein said first pivot is attached to said footstep, and said first pivot is configured to insert into one of the floor and a surface plate attached to the floor.

18. An X-ray imaging system in accordance with claim 16 further comprising a ruler attached to said footstep and configured to measure a depth of a portion of the patient below an abdomen of the patient.

19. An X-ray imaging system comprising:
   an x-ray source;
   an x-ray receptor; and
   a patient barrier, said patient barrier comprising:
      a footstep configured to support a standing patient, said footstep placed on a floor;
      a frame attached to said footstep, said frame comprising at least one of a plastic and a metal, said frame configured to separate the standing patient from the x-ray receptor;
      a support bar configured to support an arm of the standing patient and coupled to said frame such that said support bar pivots with respect to said frame;
      a hub slidably coupled within a slot defined in said frame; and
      a first pivot configured to pivot said patient barrier with respect to the floor.

* * * * *